(12) United States Patent
Pierce

(10) Patent No.: US 6,924,273 B2
(45) Date of Patent: Aug. 2, 2005

(54) CHONDROPROTECTIVE/RESTORATIVE COMPOSITIONS AND METHODS OF USE THEREOF

(76) Inventor: Scott W. Pierce, 1072 Heather Gate Ct., Lexington, KY (US) 40511

(*) Notice: Subject to any disclaimer, the term of this patent is extended or adjusted under 35 U.S.C. 154(b) by 193 days.

(21) Appl. No.: 09/967,977

(22) Filed: Oct. 2, 2001

(65) Prior Publication Data

US 2002/0068718 A1 Jun. 6, 2002

Related U.S. Application Data

(60) Provisional application No. 60/237,838, filed on Oct. 3, 2000.

(51) Int. Cl.[7] ................... A01N 65/00; A61K 31/73; A61K 38/16
(52) U.S. Cl. ..................... 514/54; 514/2; 514/56; 514/62; 424/423; 424/134.1; 424/450; 424/484; 424/756; 424/499; 424/548; 424/639; 424/486; 424/488; 536/21; 536/54; 536/18.7; 536/55.1; 536/55.2
(58) Field of Search ............... 514/54, 62, 2, 514/56; 424/423, 134.1, 450, 484, 756, 499, 548, 639, 486, 488; 536/21, 54, 18.7, 55.1, 55.2

(56) References Cited

U.S. PATENT DOCUMENTS 6,264,995 B1 * 7/2001 Newmark et al. .......... 424/725
6,346,519 B1 * 2/2002 Petrus ......................... 514/62
6,476,005 B1 * 11/2002 Petito et al. ................. 514/62

OTHER PUBLICATIONS

Horse Journal, "Hyaluronic Acid Rules In Severe Joint Problems," vol. 9, No. 5: pp 3–6 (May 2002).
Balazs, EA, et al, "Matrix engineering," Blood Coagul Fibrinolysis, vol. 2 (1): 173–8 (1991).
Shimizu, C, et al, "Histomorphometric and Biochemical Effect of Various Hyaluronans on Early Osteoarthritis," J Rheumatology, 25(9): 1813–9 (1998).
Laurent, TC, et al, "The properties and turnover of hyaluronan," Functions of the Proteoglycans, Ciba Fndtn Sympos, 124:9–29 (1986).
Tulamo, RM, et al, "Determination of concentration of hyaluronate in equine serum," Am J Vet Res, V. 51(5): 740–2 (1990).
Creamer, P, et al, Novel "Drug Treatment Strategies for Osteoarthritis," J Rheumatology, V. 20 (9):1461–3 (1993).

* cited by examiner

Primary Examiner—James O. Wilson
Assistant Examiner—Devesh Khare
(74) Attorney, Agent, or Firm—Isaac A. Angres; Susan P. Petraglia

(57) ABSTRACT

The instant invention provides a method of treating or preventing osteoarthritis, joint effusion, joint inflammation and pain, synovitis, lameness, post operative arthroscopic surgery, deterioration of proper joint function including joint mobility, the reduction or inhibition of metabolic activity of chondrocytes, the activity of enzymes that degrade cartilage, the reduction or inhibition of the production of Hyaluronic acid, said method comprising orally administering to a mammalian species a therapeutically effective amount of Hyaluronic Acid or pharmaceutically acceptable salts thereof. Additionally, compositions containing hyaluronic acid; chondroitin sulfate, and glucosamine sulfate in a paste formulation are also disclosed which can be administered on their own or can be used as a feed additive.

28 Claims, No Drawings

CHONDROPROTECTIVE/RESTORATIVE COMPOSITIONS AND METHODS OF USE THEREOF

This application claims benefit of application Ser. No. 60/237,838 filed Oct. 03, 2000.

FIELD OF INVENTION

The present invention relates to medically useful preparations based on hyaluronic acid and pharmaceutically acceptable salts thereof, a naturally-occurring substance found in animal tissue, and especially in rooster comb, vitreous humour, umbilical cords, and synovial fluid of mammals. This invention also relates to new orally administrable formulations containing hyaluronic acid. The instant invention is also directed to chondroprotective/restorative compositions containing hyaluronic acid. This invention also relates to new pharmaceutical formulations containing hyaluronic acid. The invention is further directed to a new veterinary formulations containing hyaluronic acid. This invention further relates to orally administrable veterinary formulation containing hyaluronic acid.

The present invention is also directed to veterinary formulations containing hyaluronic acid and additional bioeffective active ingredients such as bioactive agents useful in the treatment of domesticated animals especially horses. This invention also provides methods for treating horses in need of chondroprotection. The invention is further directed to pharmaceutical compositions containing hyaluronic acid, glucosamine and chondroitin. The present invention also relates to a method of treating aseptic synovitis in horses with hyaluronic acid atone or in combination with other active ingredients. More specifically, the present invention is also intended for therapeutic treatments of arthritis and related conditions using pharmaceutical compositions containing hyaluronic acid as well as other active ingredients effective in the treatment of joint diseases. The compositions of the invention are particularly useful in the veterinary field but are also very useful in treatment of humans.

This invention further relates to the oral administration of forms of hyaluronic acid and pharmaceutically acceptable salts thereof such as sodium hyaluronate, and orally administrable dosage forms containing forms of hyaluronic acid, for the prevention and/or treatment of diseases such as osteoarthritis, joint effusion, joint inflammation and pain, synovitis, and many other diseases associated with cartilage degeneration.

The instant invention also provides gels of hyaluronic acid with carboxymethylcellulose.

BACKGROUND OF THE INVENTION

Hyaluronic acid (HA) exists as a naturally-occurring polysaccharide (also known as a mucoid polysaccharide) that can be extracted from such diverse sources as rooster comb, umbilical cord, vitreous humor, synovial fluid, pathologic joints, skin and group A and C hemolytic Streptococci. The hyaluronic acid is also defined as a high viscosity naturally occurring glycosaminoglycan having a polymeric structure containing alternating N-acetyl-D-glucosamine and D-glucuronic acid monosaccharide units linked with β 1–4 bonds and the disaccharide units linked with β 1–3 glycoside bonds. It occurs usually as the sodium salt and has a molecular weight range of about 50,000 to $8 \times 10^6$ Daltons.

Hyaluronic acid is a naturally occurring glycosaminoglycan. HA is ubiquitous in the organism, with the highest concentration found in soft connective tissue and joint fluid. It is a constituent of the intercellular matrix of connective tissue that exists in almost all vertebrates. It plays an important role in a number of physiological functions, including protection and lubrication of cells, maintenance of the structural integrity of tissues, transport of molecules and cells, cell migration, cell function and differentiation, and fluid retention and regulation. The clinical benefits of intra-articular HA in the horse are well published.

Natural Hyaluronic acid is polydisperse in respect of molecular weight and is known to show excellent biocompatibility even when implanted or injected into the body by virtue of the absence of species and organ specificity. However, because of the relatively short in vivo residence time of Hyaluronic acid solution in biological applications, improvements in the persistency of Hyaluronic acid by chemical crosslinking with various chemical modifiers has been attempted to broaden its use for medical materials.

The isolation and characterization of Hyaluronic acid is described in Meyer et al, J. Biol. Chem. 107, 629 (1934); J. Biol. Chem. 114, 689 (1936); Balazs, Fed. Proc. 17, 1086 (1958); Laurent et al; Biochim. Biophys. Acta 42, 476 (1960). The structure of Hyaluronic acid was elucidated by Weissman et al, J. Am. Chem. Soc. 76, 1753 (1954) and Meyer, Fed. Proc. 17, 1075 (1958).

Hyaluronic acid is an important component of the intercellular matrix. Specifically, the highest levels are found in the eye and synovial fluid of joints. In joints, its primary role is that of lubrication, reducing pain, and inflammation. In arthritic joints HA is deficient. In healthy joints, synovial fluid supplies nutrition to the articular cartilage and has incomparable functions as a lubricant and as a shock absorber. It has been determined that its excellent viscoelasticity owes heavily to one of the main components, present therein, Hyaluronic acid. Concentration and molecular weight analyses of Hyaluronic acid demonstrated the concentration and molecular weight of Hyaluronic acid in the synovial fluid from patients with arthritis such as osteoarthritis and chronic articular rheumatism generally tended to be lower than in normal synovial fluid, and the lower concentration and molecular weight of Hyaluronic acid were closely associated with development of locomotor dysfunction and pain attributable to the weaker lubricating action and the weaker protecting action on the surface of the articular cartilage of synovial fluid.

Degradation of the structures in articular cartilage is a typical characteristic of all diseases resulting in chronic destruction of the joint structures. Examples of such disorders are rheumatoid arthritis, psoriatic arthritis, and osteoarthrosis. Also, acute inflammation of a joint is often accompanied by destruction of the cartilage, although in most cases this will not develop into the chronically destructive disease. It is not known which factors are crucial for the acutely inflamed joint to either proceed to healing or develop into the chronic process. Examples of diseases involving acute joint inflammation are yersinia arthritis, pyrophosphate arthritis, gout arthritis (arthritis urica), septic arthritis and various forms of arthritis of traumatic etiology. Among other factors potentially conducive to the destruction of articular cartilage may be mentioned, for instance, treatment with cortisone; this has been known for a long time to accelerate the degenerative process in osteoarthrosis.

Such a so-called "steroid arthropathy" occurs far too often as an undesirable side effect of intra-articular cortisone treatment and can be avoided only by providing for a sufficiently long period of rest after the treatment. Steroid arthropathy is characterized by an advanced degree of articular destruction and X-ray-detectable changes of the same type as occur in advanced degenerative articular disease (Nizolek, D H & White, K K, Cornell Vet. 1981, 71:355–75). According to what is at present accepted as an explanation of the degenerative arthropathy development following treatment with cortisone, this arthropathy is believed to be caused by a primary effect on the chondrocyte metabolism. It should be noted, however, that the actual conditions prevailing in cases of arthritis with severe inflammation of the joint are of a rather more complex character, since in those cases injection of cortisone appears to have an overall positive effect on the clinical picture.

Also, it is well known that articular cartilage is composed of about 70% of water, chondrocytes and a cartilage matrix. The major components constituting the articular matrix are collagen and proteoglycan; the proteoglycan having good water retention characteristics is contained in the network of collagen having a reticulated structure. The articular matrix is rich in viscoelasticity and has an important role in reducing the stimulus and load imposed on the cartilage in order to maintain the normal morphology and function of the articular cartilage.

Osteoarthritis and rheumatoid arthritis are representative of the diseases accompanied by the destruction of the cartilage matrix. It is thought that the destruction of the matrix in these diseases is triggered by mechanical stresses with aging in the case of osteoarthritis and by excess proliferation of the surface layer cells of the synovial membrane, pannus formation and inflammatory cell infiltration in the case of rheumatoid arthritis, and both phenomena are caused through the induction of proteases. Since the degradation of articular cartilage is progressed in the extracellular region at a neutral pH, it is said that a matrix metalloprotease (hereinafter referred to as "MMP" or "MMPs" when used as the general term) whose optimal pH is in the neutral range plays a leading role in the degradation.

No medical cure exists for osteoarthritis. The progressive degeneration of the joint due to osteoarthritis is irreversible. Present therapies are directed to palliative medical therapies to reduce inflammation and pain and surgical therapies to reconstruct an affected joint or, in severe cases, to replace the joint with an artificial, prosthetic joint.

Injection of high molecular weight Hyaluronic acid solution into diseased joints has been widely adopted as an effective measure for osteoarthritis among those articular diseases, and the source of high purity HA preparations for this purpose is cockscombs. Such HA preparations from cockscombs are biologically inherent and quite safe but usually have to be administered as frequently as several to 10 times to show significant therapeutic effect. Persistency tests on rabbits revealed that HA with a molecular weight of less than 1000000 administered into the knee joint cavities disappeared from the knee joint cavities in 1 to 3 days and suggested the need of frequent administrations (Blood Coagulation and Fibrinolysis, vol, 2(1): 173–8, (1991)).

On the other hand, the molecular weight of HA found in the living body is reported to be as high as millions to 10000000, and a crosslinked HA derivative obtained by treatment with a chemical crosslinker has been developed as a therapeutic agent for knee joints with the idea that high molecular weight HA closer to the biologically intact one is likely to have higher effect. Reportedly, the crosslinked HA persisted for a period as long as 20 to 30 days after administration into rabbit knee joint cavities in the above-mentioned persistency tests and produced sufficient effect when administered three times in clinical tests, and is practically used as a therapeutic agent for arthritis (see Blood Coagulation and Fibrinolysis, ibid.; and Journal of Rheumatology vol. 25(9): 1813–9 (1998)).

A need exists for an effective palliative medication for the treatment of osteoarthritis and other joint diseases which is both safe and effective when used for both short-term and long-term therapy and which can be administered orally.

OBJECTS OF THE INVENTION

It is a first object of the present invention to provide a method for treating mammals having joint diseases by oral administration of hyaluronic acid and salts thereof.

It is another object of the instant invention to provide novel chondroprotective/restorative compositions.

A further object of the invention is to provide a novel chondroprotective/restorative composition containing hyaluronic acid in paste or gel form.

A still further object of the invention is to provide novel chondroprotective/restorative compositions containing hyaluronic acid, glucosamine sulfate and chondroitin sulfate.

An additional object of the invention is to provide chondroprotective/restorative compositions containing hyaluronic acid and bioeffective materials.

A still additional object of the invention is to provide chondroprotective/restorative compositions containing hyaluronic acid, vitamins and minerals.

An additional object of the present invention is provide chondroprotective/restorative compositions containing hyaluronic acid, vitamins and minerals.

Another main object of the present invention is to provide an aqueous gel containing hyaluronic acid and molasses.

Another object of the present invention is to provide paste formulations containing hyaluronic acid, glucosamine sulfate and molasses.

An additional object of the invention is to provide gel formulations containing HA in a carboxymethylcellulose base.

A further object of the invention is to provide animal feeds containing hyaluronic acid.

These and other objects of the invention will become apparent from the description hereinafter.

SUMMARY OF THE INVENTION

The present invention provides a method for treating or preventing osteoarthritis, joint effusion, joint inflammation and pain, synovitis, lameness, post operative arthroscopic surgery, deterioration of proper joint function, the reduction or inhibition of metabolic activity of chondrocytes, the activity of enzymes that degrade cartilage, the reduction or inhibition of the production of hyaluronic acid, said method comprising orally administering to a mammalian species a therapeutically effective amount of hyaluronic acid or pharmaceutically acceptable salts thereof.

The invention is also directed to a Chondroprotective/Restorative composition comprising Hyaluronic Acid or its pharmaceutically acceptable salts and optionally a pharmaceutically acceptable carrier.

The instant invention also provides a Chondroprotective/Restorative composition comprising: (a) an effective amount of Glucosamine sulfate; (b) an effective amount Hyaluronic Acid or pharmaceutically acceptable salts thereof; and (c) optionally a pharmaceutically acceptable carrier.

Additionally, the invention provides a Chondroprotective/Restorative composition comprising: (b) an effective amount of Chondroitin sulfate; (b) an effective amount of Hyaluronic Acid or pharmaceutically acceptable salts thereof; and (c) optionally a pharmaceutically acceptable carrier.

The instant invention further provides a Chondroprotective/Restorative composition comprising: (a) an effective amount of Glucosamine sulfate; (b) an effective amount of Chondroitin sulfate; (c) an effective amount of Hyaluronic Acid or pharmaceutically acceptable salts thereof; and (d) optionally a pharmaceutically acceptable carrier.

The Chondroprotective/Restorative compositions of the invention further include nutritionally effective amounts of a supplement selected from the group consisting of vitamin A, D and E, ascorbic acid, biotin, panthothenic, choline, niacin, pyridoxine, riboflavin, thiamine, calcium, phosphorus, NaCl, copper, iron, manganese, iodine, zinc and combinations thereof.

The invention is also directed to an animal feed having Chondroprotective/Restorative benefits comprising: (a) a nutritionally effective feed base selected from the group consisting of grains, proteins and fats; and (b) an effective amount of Hyaluronic Acid or pharmaceutically acceptable salts thereof.

Furthermore, the invention relates to a therapeutic Chondroprotective/Restorative composition comprising: (a) Hyaluronic Acid or its pharmaceutically acceptable salts; (b) a therapeutic drug; and (c) optionally a pharmaceutically acceptable carrier.

The invention is also directed to a Chondroprotective/Restorative composition in paste form comprising: (a) an effective amount of Hyaluronic Acid or its pharmaceutically acceptable salts; and (b) a sufficient amount of molasses to make a paste.

Additionally, the invention also relates to a Chondroprotective/Restorative composition in gel form comprising: (a) an effective amount of Hyaluronic Acid or its pharmaceutically acceptable salts; and (b) a sufficient amount of carboxymethylcellulose to make a paste.

DETAILED DESCRIPTION OF INVENTION

In the first preferred embodiment of the invention, there is provided viscosupplementation of joints by oral administration of sodium hyaluronate (HA) to mammals and more in particular to racing thoroughbreds. Applicant's conducted a double blind placebo-controlled study wherein ten horses were randomly chosen and given an oral gel (also known as Conquer and containing 100 mg of hyaluronic acid) for 59 days. Every parameter used to measure soundness was improved in the HA treated group. Also, every parameter used to measure routine maintenance of the racing Thoroughbred was improved in the HA treated group. All horses in the treated group with pre-existing conditions showed clinical improvement during the study.

In conducting our study, ten actively training Thoroughbreds were randomly selected. Five were given a placebo gel and five were given a gel containing 100 mg of Sodium Hyaluronate. The duration of the study was 59 days. The ages of the horses varied: one two-year old, five three-year olds, two four-year olds, and two five-year olds. Because the half-life of circulating HA is two days or less, the horses were given 100 mg once daily. Upon completion of the study, training and veterinary records were evaluated. Number of days to the track was compared to number of days walked. In addition, horses receiving NSAIDS during the study for any reason were recorded as were horses examined for any lameness. Horses were evaluated weekly for joint effusion, pain on flexion, and signs of lameness. Horses radiographed due to lameness were recorded. Horses with pre-existing conditions were monitored and periodically evaluated.

The results of oral administration of HA are listed in Tables 1 and 2 below. Treated horses went to the track more days than the non-treated group (40 versus 32). Horse 110, of the non-treated group sustained a cortical stress fracture 33 days into the study. With this non-articular injury removed from the study, the average days to the track of the non-treated group changes from 32 to 35 days. All of the non-treated horses were examined for lameness at some time during the study. None of the treated horses were examined for lameness. All horses in the treated group with pre-existing conditions improved. NSAIDS, primarily phenylbutazone, was used at some time during the study in 5 of 5 of the non-treated horses. Less was used in the treated group, 2 of 5. None of the treated group were radiographed during the study while 3 of 5 of the non-treated group had radiographs taken. More horses developed new signs of synovial effusion in the non-treated group, 3 of 5, than in the treated group, 1 of 5. The treated group required less bandaging (3 of 5) than the non-treated group (5 of 5).

TABLE 1

| Horses | Age | Sex | Days To Track | Days Walked | Examined For Lameness | NSAIDS | Radio- graphed |
|---|---|---|---|---|---|---|---|
| TREATED HORSES | | | | | | | |
| 101 | 5 | G | 45 | 14 | NO | YES | NO |
| 102 | 2 | F | 41 | 18 | NO | NO | NO |
| 105 | 4 | M | 38 | 21 | NO | NO | NO |
| 106 | 5 | M | 31 | 28 | NO | NO | NO |
| 109 | 4 | M | 46 | 13 | NO | YES | NO |
| TREATED TOTALS | | | | | | | |
| N/A | N/A | N/A | 201 (Ave. 40) | 94 (Ave. 19) | NONE | 2/5 | NONE |
| NON-TREATED HORSES | | | | | | | |
| 103 | 3 | C | 44 | 15 | YES | YES | NO |
| 104 | 3 | C | 19 | 40 | YES | YES | YES |
| 107 | 3 | F | 43 | 16 | YES | YES | NO |
| 108 | 3 | C | 34 | 25 | YES | YES | YES |
| 110* | 3 | C | 19 | 40 | YES | YES | YES |
| NON-TREATED TOTALS | | | | | | | |
| N/A | N/A | N/A | 159 (Ave. 32) | 136 (Ave. 27) | 5/5 | 5/5 | 3/5 |

*Horse 110 sustained a cortical stress fracture 33 days into the study. By removing him from the totals the average days to the track becomes 35 days instead of 32 days.

TABLE 2

| Horse | Pre-existing Condition | Condition | Improved | New Joint Effusion During Study | Location |
|---|---|---|---|---|---|
| TREATED HORSES | | | | | |
| 101 | YES | Osslets | YES | NO | N/A |
| 102 | NO | N/A | N/A | YES | CARPUS |
| 105 | YES | Severe T Sheath Eff. | YES | NO | N/A |

TABLE 2-continued

| Horse | Pre-existing Condition | Condition | Improved | New Joint Effusion During Study | Location |
|---|---|---|---|---|---|
| 106 | YES | Chronic Osslets | YES | NO | N/A |
| 109 | YES | Osslets | YES | NO | N/A |
| NON-TREATED HORSES | | | | | |
| 103 | YES | Stiffness Behind | YES | YES | Carpus |
| 104 | NO | N/A | N/A | NO | N/A |
| 107 | NO | N/A | N/A | YES | Fetlocks |
| 108 | YES | Left Front Soreness | NO | YES | Stifles |
| 110 | NO | N/A | N/A | NO | N/A |

As can be appreciated from Tables 1 and 2, horses maintained on a daily dose of oral sodium hyaluronate showed improvement of all soundness characteristics measured. Horses with pre-existing synovitis improved while on oral HA. Accordingly, the data suggests that Oral sodium hyaluronate appears to be effective in preventing lameness in the racing Thoroughbred. None of the horses in the treated group were examined for lameness while in the non-treated group, two horses developed mild forelimb lameness which were subtle and difficult to diagnose with diagnostic nerve blocks, one horse became painful in his back and front feet and a fourth horse became acutely lame after a race. This lameness could not be completely diagnosed with nerve blocks therefore a bone scan was performed. Results showed increased uptake in the left carpus, left front fetlock, and solar margins of the foot. After resting about 30 days, this horse resumed training. The present invention provides evidence of HA's ability to have a performance enhancing effect in the racing Thoroughbred when used orally. In addition, oral administration of HA is effective in the treatment of synovitis associated with osteoarthritis.

In the second preferred embodiment of the invention, an oral preparation containing sodium hyaluronate was evaluated in the treatment of aseptic synovitis. Horses chosen had clinical signs of joint disease and were treated with 100 mg of Sodium Hyaluronate, 1 g Chondroitin sulfate, and 200 mg Vitamin C for 30 days.

In conducting the above study, six adult horses were administered 100 mg of sodium hyaluronate, 1 g of Chondroitin sulfate, and 200 mg Vitamin C daily in an oral preparation. The horses were treated for 30 days and were monitored continuously. Clinical evaluations were performed on day 1, day 30, and at day 45 (two weeks after discontinuation of treatment). Clinically, four horses had significant aseptic syovitis of the metacarpolphalangeal joints. One horse suffered from villinodular synovitis and one horse had degenerative joint disease of the proximal interphalangeal joint (ringbone). The results of the study are summarized in Table 3 below.

TABLE 3

| Symptom | Day 1 | Day 30 | Day 45 |
|---|---|---|---|
| Overall evaluation | Inflammed effusion Pain on flexion | Improved in 5 of 6 horses | Improved in 5 of 6 horses |
| Swelling effusion | 6 of 6 horses | Improved in 5 of 6 horses | Improved in 5 of 6 horses |
| Joint Pain | 6 of 6 horses | Improved in 5 of 6 horses | Improved in 5 of 6 horses |
| Lameness | Grade 1 or 2 lame in 6 of 6 horses | Sound in 5 of 6 horses | Sound in 5 of 6 horses |
| Range of Motion | Decreased in 6 of 6 horses | Improved in 5 of 6 horses | Improved in 5 of 6 horses |

As can be appreciated from Table 3, significant improvement was seen in five of six horses. The amount of synovial effusion and inflammation decreased in all but one case. There was improvement of lameness and decreased pain on flexion. The horse diagnosed with degenerative joint disease of the proximal interphalangeal joint showed no improvement. Oral delivery of sodium hyaluronate is a viable alternative for treatment of synovitis in the horse. It is very safe with no side effects being reported in this study.

In a third embodiment of the invention, another oral gel consisting of 100 mg per dose of sodium hyaluronate was evaluated. Horses chosen had significant signs of synovitis and joint pain. Treatment was continued for 21 days. In conducting the study, four weanling Thoroughbred foals and one three year old Thoroughbred racehorse were given 100 mg daily of sodium hyaluronate in a gel formulation. All horses were diagnosed with moderate to severe synovitis of the metacarpolphalangeal joints. Two of the foals and the three year old racehorse had moderate to severe effusion and pain in both fore fetlocks while the other two had marked synovitis of all four fetlocks. Three of the foals were Grade 1/5 lame and one foal was grade 2/5 lame at a walk and trot. The race horse was not lame at a walk or trot but was painful on flexion. All foals were very painful on flexion and lameness was significantly worsened following fetlock flexion tests. Radiographs of the affected fetlocks did not reveal any bony abnormalities. Treatment was continued for 21 days and all horses wee evaluated weekly. No other treatments were administered during this time.

The results are summarized in Table 4. In one foal with effusion in all four fetlocks (Grade 1/5 lame), significant improvement was seen after seven days of treatment. Synovial effusion had decreased and the foal was sound at a walk and trot. Slight lameness was observed after fetlock flexion. By week two, this foal's joints were considered normal and no pain on flexion or lameness could be detected. In the second foal with marked effusion in all four fetlocks (Grade 2/5 lame), moderate synovial effusion was still present at seven days. After fetlock flexion, this foal's lameness worsened to a Grade 4/5. At the $14^{th}$ day exam, significant improvement was observed. The amount of joint swelling had decreased dramatically and the foal's lameness was improved. There was lameness pain on flexion and the lameness after fetlock flexion improved to a Grade 1/5. At the $21^{st}$ day exam, the joints were considered normal and the foal was sound at a walk and trot. The third and fourth foals with synovial effusion in the front fetlocks showed significant improvement in seven days. They continued to have slight pain on flexion and slightly lame after fetlock flexion. By 14 days these foals had slight effusion but were sound and negative to fetlock flexion. At the $21^{st}$ day exam they were considered normal. The 3 year old racehorse had a significant decrease in synovitis at day 7. By the $14^{th}$ day there was slight effusion and no pain on flexion. At 21 days, there continued to be slight effusion but no lameness or pain on flexion.

TABLE 4

| Horse | Day 1 | Day 7 | Day 14 | Day 21 |
|---|---|---|---|---|
| #1 | Moderate effusion in all four fetlocks. Grade 1/5 lame/ Moderate pain on flexion | Mild effusion in all four feflock/Sound/Slight pain on flexion | No effusion. Sound/ No pain on flexion | No effusion. Sound/No pain on flexion |
| #2 | Severe effusion in all four Fetlocks Grade 2/5 lame, Severe pain on flexion | Moderate effusion in all four fetlocks. Grade 1/5 lame fetlocks. Moderate pain on flexion | Mild effusion in front Grade 1/5 lame Moderate pain on flexion | Slight effusion in front fetlocks, Sound, Slight pain on flexion |
| #3 | Moderate effusion on front Fetlocks. Grade 1/5 lame, Mild pain on flexion | Mild effusion in front Fetlocks. Sound, Mild pain on flexion | Slight effusion in front Fetlock. Sound, No pain on flexion | No effusion, Sound No pain on flexion |
| #4 | Moderate effusion on front Fetlocks. Grade 1/5 lame, Mild pain on flexion | Mild effusion in front Fetlocks. Sound, Mild pain on flexion | Slight effusion in front Fetlock. Sound, No pain on flexion | No effusion, Sound No pain on flexion |
| #5* | Moderate effusion in front Fetlocks. No Lameness, Mild pain on flexion | Mild effusion in front Fetlocks. Sound, slight pain on flexion | Slight effusion in front Fetlock. Sound, No pain on flexion | No effusion, Sound No pain on flexion |

*Three year old racehorse

In a further clinical trial of the invention, 24 hockey players were treated via oral administration with a combination of sodium hyaluronate and chondroitin sulphate in gel form as exemplified in Example 16 for three months. The dosage levels were 0.1–0.5 mg/Kg of body weight. A greater than sixty five percent improvement in their knee joint was observed.

Additionally, 27 human patients were treated via oral administration with a combination of sodium hyaluronate and chondroitin sulphate in gel form as exemplified in Example 16 for three months after knee surgery. The dosage levels were 0.1–0.5 mg/Kg of body weight. At least a 58% improvement was observed on their knee joints.

It should be noted that in treating mammals the recommended daily dosage for hyaluronic acid is about 0.1 to 0.5 mg/Kg of body weight. Accordingly, for a human the dosage ranges can be from 7 to 40 mg; while for a horse the range can be from 50–250 mg and for a dog the ranges would be 2–8 mg.

In a fourth embodiment, the invention also provides chondroprotective and restorative compositions which are very useful for oral administration. The compositions contain 10 to 2000 mg of hyaluronic acid and optionally a pharmaceutically acceptable carrier.

In a fifth embodiment, the present invention relates to chondroprotective and restorative compositions useful for oral administration containing: (a) 0.01–10 wt % hyaluronic acid or its pharmaceutical acceptable salts; (b) optionally 20–60 wt % glucosamine or its pharmaceutically acceptable salts; (c) optionally 1–15 wt % chondroitin or its pharmaceutical acceptable salts; (d) optionally nutritionally effective (recommended daily allowance) amounts of a supplement selected from the group consisting of vitamin A, D and E, ascorbic acid, B complex, B12, B1, biotin, panthothenic, choline, niacin, pyridoxine, riboflavin, thiamine, calcium, phosphorus, NaCl, copper, iron, manganese, iodine, zinc and combinations thereof; (e) optionally effective amounts of a bioactive agent or drug; and (f) optionally a pharmaceutically or nutritionally acceptable carrier.

The pharmaceutical acceptable salts of hyaluronic acid include the alkali metal salts as well as the alkaline earth metal salts. Typical salts include sodium hyaluronate, potassium hyaluronate, magnesium hyaluronate and calcium hyaluronate. The preferred salt in the compositions of the invention is sodium hyaluronate.

The pharmaceutically effective salts of glucosamine are selected from the group consisting of glucosamine chloride, glucosamine bromide, glucosamine iodide and glucosamine sulfate. Similarly, with chondroitin the same type of salts are usable i.e., chondroitin chloride, chondroitin bromide, chondroitin sulfate and chondroitin iodide.

The bio-effective or drug component of the invention is selected from the group consisting of angiotensin converting enzyme inhibitors, anti-asthmatics, anti-cholesterolemics, anti-convulsants, anti-depressants, anti-diarrhea preparations, anti-infectives, anti-inflammatory agents, anti-nauseants, anti-stroke agents, anti-tumor drugs, anti-tussives, anti-uricemic drugs, amino-acid preparations, antiemetics, antiobesity drugs, antiparasitics, antipyretics, appetite stimulants, cerebral dilators, chelating agents, cholecystokinin antagonists, cognition activators, deodorants, dermatological agents, diabetes agents, diuretics, erythropoietic drugs, fertility agents, synthetic hormones, laxatives, mineral supplements, neuroleptics, neuromuscular agents, peripheral vaso-dilators, prostaglandins, vaginal preparations, vaso-constrictors and vertigo agents.

The bio-effecting agent is selected from the group consisting of acetaminophen, acetic acid, acetylsalicylic acid, buffered acetylsalicylic acid, albuterol, albuterol sulfate, ethanol isopropanol, allantoin, aloe, aluminum acetate, aluminum carbonate, aluminum chlorohydrate, aluminum hydroxide, alprozolam, amino acids, aminobenzoic acid, amoxicillin, ampicillin, amsacrine, amsalog, anethole, aspartame, atenolol, bacitracin, balsam peru, beclomethasone dipropionate, benzocaine, benzoic acid, benzophenones, benzoyl peroxide, biotin, bisacodyl, bornyl acetate, bromopheniramine maleate, buspirone, caffeine, calamine, calcium, calcium carbonate, calcium casinate, calcium hydroxide, camphor, captopril, cascara sagrada, castor oil, Cephalosporins, cefaclor, cefadroxil, cephalexin, cetylalcohol, cetylpyridinium chloride, chelated minerals, chloramphenicol, chlorcyclizine hydrochloride, chlorhexidine gluconate, chloroxylenol, chloropentostatin, chlorpheniramine maleate, cholestyramine resin, choline bitartrate, cimetidine hydrochloride, cinnamedrine hydrochloride, citalopram, citric acid, Clenbuterol, cocoa butter, cod liver oil, codeine and codeine phosphate, clonidine, clonidine hydrochloride, clorfibrate, ciprofloxacin HCl, cyanocobalamin, cyclizine hydrochloride, DMSO, danthron, Dantrium, dexamethazone, dexbrompheniranime maleate, dextromethorphan hydrobromide, diazapam, dibucaine, diclofenac sodium, digoxin, diltiazem, dimethicone, dioxybenzone, diphenbydramine citrate, diphenhydramine hydrochloride, docusate calicum, docusate potassium, docusate sodium, doxycycline hyclate, doxylamine succinate, efaroxan, enalapril, enoxacin, erythromycin, estropipate, ethinyl estradiol, ephedrine, epinephrine bitartrate, erythropoietin, eucalyptol, ferrous fumarate, ferrous gluconate, ferrous sulfate, folic acid, fosphenytoin, Flunixin Meglumine, fluoxetine HCl, furosemide, gabapentan, gentamicin, Gentocin sulfate, gemfibrozil, glipizide, glycerin, glyceryl stearate, griseofulvin, guaifenesin, hexyiresorcinol, hydrochlorothiaxide, hydrocodone bitartrate, hydrocortisone, hydrocortisone acetate, 8-hydroxyquinoline sulfate, ibuprofen, indomethacin, inositol, insulin, iodine, ipecac, iron, isoxicam, ketamine, Ketofin, koalin, lactic acid, lanolin, lecithin, lidocaine, lidocaine hydrochloride, lifinopril, liotrix, lovastatin, MSM (methylsulfonylmethane), magnesium carbonate, magnesium hydroxide, magnesium salicylate, magnesium trisilocate, mefenamic acid, meclofenanic acid, meclofenamate sodium, medroxyprogesterone acetate, methenamme mandelate, Methocarbamol, menthol, meperidine hydrochloride, metaproterenol sulfate, methyl nicotinate, methyl salicylate, methylcellulose, methsuximide, metromidazole, metromidazole hydrochloride, metoprolol tartrate, miconazole nitrate, mineral oil, minoxidil, morphine, naproxen, naproxen sodium, nifedipine, neomycin sulfate, Neomycin-Bacitracin, niacin, niacinamide, nicotine, nicotinamide, nitroglycerin, nonoxynol-9, norethindone, norethindone acetate, nystatin, octoxynol, octyl dimethyl PABA, octyl methoxycinnamate, omega-3 polyunsaturated fatty acids, omeprazole, oxolinic acid, oxybenzone, oxtriphylline, para-aminobenzoic acid (PABA), padimate 0, paramethadione, Penicillin, pentastatin, peppermint oil, pentaerythriol tetranitrate, pentobarbital sodium, pheniramine maleate, phenobarbital, phenol, phenolphthalein, phenylbutazone, phenylephrine hydrochloride, phenylpropanolamine, phenylpropanolamine hydrochloride, phenytoin, phenelzine sulfate, pirmenol, piroxicam, polymycin B sulfate, potassium chloride, potassium nitrate, prazepam, prednisone, prednisolone, procainamide hydrochloride, procaterol, propoxyphene, propoxyphene HCl, propoxyphene napsylate, pramiracetin, pramoxine, pramoxine hydrochloride, propronolol HCl, pseudoephedrine hydrochloride, pseudoephedrine sulfate, pyridoxine, quinapril, quinidine gluconate, quinestrol, ralitoline, ranitadine, resorcinol, riboflavin, salicylic acid, sesame oil, shark liver oil. simethicone, sodium bicarbonate, sodium citrate, sodium fluoride, sodium monofluorophosphate, Sulfa-drugs, sulfanethoxazole, sulfur, tacrine, tacrine HCl, theophylline, terfenidine, thioperidone, trimetrexate, triazolam, timolol maleate, tretinoin, tetracycline hydrochloride, tolmetin, tolnaftate, triamcinilone, triclosan, triprolidine hydrochloride, undecylenic acid, vancomycin, verapamil HCl, vidaribine phosphate, vitamin A, vitamin B, vitamin C, vitamin D, vitamin B, vitamin K, witch hazel, xylometazoline hydrochloride, zinc, zinc sulfate, and zinc undecylenate.

The compositions of the invention can be made in paste form, gel forms, tablets and capsules. The paste form of the invention contains molasses in an amount effective to form a paste.

The gel forms of the invention are formed by mixing the actives with water and then adding a gelling agent. The gelling agent is selected from the group consisting of cellulose or a cellulose derivative in an amount of from 0.5 to 5 wt. % and said cellulose derivative is selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, cellulose gum carboxymethylcellulose and sodium carboxymethylcellulose.

In making the compositions of the invention, the active materials will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methylcelluse, methyl and propylhydroxybenzoates, talc, magnesium stearate and mineral oil. The formulations can additionally include lubricating agents wetting agents, emulsifying and suspending agents, preserving agents, sweetening agents or flavoring agents. The compositions may be formulated so as to provide rapid, sustained or delayed release of the active ingredient after administration to the patient by employing procedures well-know in the art.

In a sixth embodiment of the invention, an animal feed is provided having chondroprotective and restorative properties. The animal feed base of the present invention comprises farinaceous material selected from the group consisting of wheat, wheat flour, wheat meal by-products and corn in an amount of 25 to 70% by weight based on the total weight of the feed, further comprising proteinaceous material selected from the group consisting of soybean meal, soy flour, peanut meal, cottonseed meal, safflower seed meal in an amount of from 5 to 40% by weight based on the total weight of the feed, further comprising fibrous material selected from the group consisting of soy hulls, cottonseed hulls, rice hulls in an amount of from about 2 to 35% by weight based on the total weight of the feed, further comprising nutritional supplements selected from the group consisting of vitamin A, D and E, ascorbic acid, biotin, panthothenic, choline, niacin, pyridoxine, riboflavin, thiamine, calcium, phosphorus, NaCl, copper, iron, manganese, iodine, zinc and combinations thereof, in an amount of from 3 to 4% by weight based on the total weight of the feed, further comprising a vegetable oil coating, said oil selected from the group consisting of soybean oil, corn oil, safflower oil, cottonseed oil, peanut oil, in an amount of from 1 to 15% by weight based on the total weight of the feed.

The above feed base is blended with a paste having the following formulation ranges: (a) 0.01–10 wt % hyaluronic acid or its pharmaceutical acceptable salts; (b) optionally 20–60 wt % glucosamine or its pharmaceutically acceptable salts; (c) optionally 1–15 wt % chondroitin or its pharmaceutical acceptable salts; (d) optionally nutritionally effective (recommended daily allowance) amounts of a supplement selected from the group consisting of vitamin A, D and E, ascorbic acid, B complex, B12, B1, biotin, panthothenic, choline, niacin, pyridoxine, riboflavin, thiamine, calcium, phosphorus, NaCl, copper, iron, manganese, iodine, zinc and combinations thereof; (e) optionally effective amounts of a bioactive agent or drug; and (f) 15–35 wt % molasses. The feed of course is formulated in way to provide optimum nutrition and optimum chondroprotection depending on the specific animal and their current state of health.

The present invention is the most unique chondoprotective/restorative agent available. The molasses flavored oral paste provides a practical, efficient, and effective means of administration orally or top dressing feed. When added to the feed, the molasses base binds to the feed to insure total consumption. When necessary, an easy measurable dose can be administered orally. The highly palatable formulation of the invention is the first to combine high levels of Glucosamine sulfate (GS) with Chondroitin sulfate (CS) and Hyaluronic Acid (HA) in an easy to absorb, low molecular weight formula. It has also been shown that liquid or paste forms are more readily absorbed than encapsulated or powder forms. The chondroprotective/restorative agent of the invention enhance chondrocyte synthesis, increase synthesis of hyaluronic acid, inhibit enzymes that degrade cartilage, and reduce pain and synovitis. It must also slow down or reverse progression of the disease. The present invention, with its unique combination of GS, CS, and HA is the closest yet to satisfying these criteria.

These three substances are the three connective tissue molecules needed to rebuild and synthesize new tissue. Connective tissue is comprised mainly of collagen and proteoglycans. Proteoglycans provide the framework for collagen and hold water, enhancing the flexibility and resistance to compression needed to counteract physical stress. The building blocks for all proteoglycans are amino sugars. Glucosamine is the building block needed as the precursor for all subsequent amino sugar synthesis. The formation of N-acetylglucosamine, chondroitin sulfate, and hyaluronic acid require glucosamine for their synthesis. In fact, glucosamine makes up 50% of the hyaluronic acid molecule.

Glucosamine sulfate along with Chondroitin sulfate have become very popular supplements administered in the treatment of degenerative joint disease. Recent studies have questioned whether the combination produces better results than Glucosamine sulfate alone. Also there is much debate over which glucosamine salt is preferred. Embodiments of the present invention utilize Glucosamine sulfate as its source of Glucosamine. Most of the past and present research has been performed on the sulfated form. There is evidence that suggests that a component of the activity of GS and CS is related to the sulfate residues found in these compounds. Sulfur is an essential nutrient for the stabilization of the connective tissue matrix. It has been proposed that the sulfate molecules of GS and CS contribute to the therapeutic benefits of the compounds in degenerative joint disease. If this is true, it would suggest that GS, as opposed to N-acetylglucosamine and glucosamine HCI, is the best form of glucosamine supplementation. Recently, it has been shown that high-dose glucosamine may provide rapid symptomatic benefit and in the long term repair of damaged cartilage. The high dose of glucosamine not only promotes synthesis of cartilage proteogycans, but stimulates synovial production of hyaluronic acid. This would explain the anecdotal reports that a high dose of glucosamine is beneficial.

As previously explained, the present invention comprises a highly palatable formulation, which is the first to combine high levels of Glucosamine sulfate (GS) with Chondroitin sulfate (CS) and Hyaluronic Acid (HA) in an easy to absorb, low molecular weight formula.

Glucosamine, which is formed in the body as glucosamine 6-phosphate is the most fundamental building block required for the biosynthesis of the classes of compounds such as glucolipids, glycoproteins, glycosamineglycans, hyaluronate, and proteoglycans. Directly or indirectly, glucosamine plays a role in the formation of articular surfaces, tendons, ligaments, synovial fluid, skin, bone, heart valves, blood vessels and mucus secretions of the digestive, respiratory and urinary tracts. Glucosamine sulfate is greater than 90% absorbed and is quickly incorporated into articular cartilage following oral administration.

In one study, no LD50 was established for Glucosamine sulfate since even at very high levels (5000 mg/kg orally) there was no mortality in mice and rats. While treatment with GS does not produce the initial dramatic reductions in pain normally associated with NSAIDs, its ability to reduce pain is consistent and progressive throughout the course of it's administration, resulting in a long-term improvement in the condition. Glucosamine is a small molecule and is very soluble in water.

Chondroitin Sulfate achieves benefits much more slowly than glucosamine. Chondroitin bioavailability following oral administration is around 15%. Because of its lower bioavailability, the time needed to see a clinical response is lengthened. Chondroitin improves joint fluidity by drawing water to the cartilage tissue. When this water is drawn into the cartilage, it is accompanied by nutrients which are supplied to the cartilage. Additionally Chondroitin helps fight enzymes that inhibit transportation of nutrients into these tissues as it prevents other enzymes from tearing down cartilage tissue. Furthermore, Chondroitin, like Glucosamine, promotes the product of key cartilage components such as proteoglycans and it also prevents abnormal cell death.

Hyaluronic acid is one of many glycosaminoglycans of physiological significance. Other are Chondroitin sulfate, Heparin sulfate, and Dermatan sulfate. The HA molecule is very similar to that of Chondroitin sulfate. In numerous studies, the oral absorption of CS, HS and DS have been well documented. The bioavailabilities range from 15–20%. Hyaluronic acid has been shown to be absorbed through skin and reach the dermal lymphatics. Also, high levels of hyaluronan has been detected in the intestinal lymphatics. In addition, studies have been performed to determine the effects of HA secreted in saliva. Others have looked at hyaluronic acid production by oral epithelial cells. According to the present invention, there is a beneficial effect when Glucosamine sulfate, Chondroitin sulfate, and Hyaluronic acid are administered orally. Generally, the oral administration of a gel or paste form composition of HA, GS, and CS has a quicker clinical response than is produced when each component of the composition is given individually. A significant difference is an acute or a rapid relief from joint pain, inflammation and swelling achieved by oral administration of the composition. A dramatic improvement over seven to ten days is achieved with the present embodiment, whereas it usually takes weeks for that effect to occur when GS and CS are administered without HA. Another beneficial embodiment is an oral preparation for oral administration of an effective chondroprotective/restorative amount of HA to, for example, an equine. The administration of the HA composition orally and having a clinical effect eliminates more invasive procedures. Other ways to give HA would be more invasive, such an injection by IV or other administration into the joints. Thus, the embodiments of the present invention include oral preparations that are administrable by less invasive routes and which also may provide the sole clinically effective way to orally administer HA when other routes (e.g., injection) are not possible.

Another benefit is that embodiments of the present invention, with its high dose of Glucosamine sulfate, Hyaluronic acid, and Chondroitin sulfate, appears to have a synergistic effect which hastens the clinical response.

One further embodiment of the present invention is a unique formulation that combines Glucosamine sulfate, Chondroitin sulfate, and Hyaluronic acid into a paste formulation for direct oral administration or top dressing feed. This is the only product available which combines these three substances which are critical for cartilage metabolism and production of synovial fluid. Also, this embodiment is the only oral paste formulation available for any one of these supplements. Early clinical trials have shown that when the three products are combined, they have a synergistic effect. The clinical effects have been impressive. Data has shown a quicker clinical response when GS, CS, and HA are combined than when they are used individually. Conditions in which embodiments of the present invention would be beneficial:

1) Osteoarthritis
2) Joint effusion
3) Joint inflammation and pain
4) Post operative arthroscopic surgery
5) Restoring proper joint function
6) Promote metabolic activity of chondrocytes (cartilage producing cells)
7) Inhibit enzymes that degrade cartilage
8) Stimulate the production of Hyaluronic acid.

Embodiments of the present invention possess the following advantages:

1) Only paste formulation
2) Only combination of GS, CS, HA in a paste formulation
3) Only oral paste form of Glucosamine
4) Only oral paste form of Chondroitin
5) Only oral paste form of Hyaluronic acid
6) Only oral paste in a molasses flavored base
7) Only oral gel in apple flavored carboxymethylcellulose base.

One embodiment of the present invention possesses a molasses flavor. Other flavors would include apple, cherry, and any other palatable flavor.

One embodiment of the present invention comprises the following:

|  | Wt % |
| --- | --- |
| Glucosamine sulfate | 46.03 |
| Chondroitin sulfate | 4.60 |
| Sodium Hyaluronate | 0.18 |
| Manganese sulfate | 0.18 |
| Powdered sugar | 8.70 |
| Xanthan gum | 0.10 |
| Molasses | 25.00 |
| Water | 14.00 |
| Glycerine | 0.70 |
| Corn Starch | 0.30 |
| Sodium Benzoate | 0.50 |

Embodiments of the present invention in a paste formulation has many advantages. When adding to feed, the formulation will stick to grain to insure total consumption. Embodiments of the paste formulation can be given orally (direct administration) or added to feed—depending on management of animals (e.g., whether turned out in field vs. stall confinement). Other advantages include the following:

1) Better absorption with liquids
2) Molasses flavored paste—more palatable
3) Apple flavored gel—more palatable
4) Sticky consistency—animal cannot spit product from mouth which insures total dose
5) Syringe dose insures more accurate dose.
6) Brown sugar included—more palatable Effects of GS vs CS:

Glucosamine Sulfate:

1) Enhances chondrocyte synthesis
2) Enhances synthesis of hyaluronic acid
3) Reduces joint pain
4) Reduces synovitis Chondroitin Sulfate:

1) Also helps with chondrocyte synthesis
2) CS has been found to inhibit degradative enzymes in cartilage
3) CS strengthens and enhances vessels that feed joints or supply them with nutrients by reducing arterial plaque and clear cholesterol deposits.
4) Reduces joint pain and improves joint mobility.
5) Reduces synovitis associated with joint arthritis.

Neither GS or CS fulfills the quest for the ideal chondroprotective/restorative agent separately but when combined they appear to provide the necessary components for the health and wellbeing of the joint. Hyaluronic acid complements the combination by helping to restore the HA levels needed for joint health and lubrication which are decreased when synovitis is present.

Hyaluronic acid is a glycosaminoglycan. Other glycosaminoglycans are Chondroitin sulfate, Heparin sulfate, and Dermatan sulfate. The most abundant GAG is Chondroitin sulfate. The three related GAGs have been found to be absorbed orally. Because of their chemical similarities and the clinical reports of improvement of synovitis, HA has a synergistic effect with GS and CS when given orally. This effect is observed as a more rapid clinical response than when GS and CS are given individually.

Clinically, responses are seen in 7 to 10 days vs three to four weeks or not at all when GS and CS are given without HA. Therefore, we have seen a dramatic decrease in synovitis when HA is combined with GS and CS. This leads us to conclude that HA is absorbed orally and effective either alone or in combination with GS and CS. Therefore, an additional embodiment of the invention comprises a composition including HA and any acceptable carrier, such as the paste formulation disclosed herein and any other liquid, powder, gel or similar type carrier.

Another embodiment of the invention includes a paste formulation containing the active component isoxuprine. Isoxuprine is a vasodilator and is utilized in treatment of many afflictions including the treatment of navicular disease. One effect of isoxuprine is that it stimulates the vasodilator nerves, such as the vaso-inhibitory and vasohypotonic nerves, and causes dilation or relaxation of the blood vessels. Administration of isoxuprine to a patient, such as an animal, in the form of a paste is beneficial to ensure adequate administration.

The present invention is illustrated by the following Examples, but should not be construed to be limited thereto. In the Examples, "part" and "%" are all part by weight or % by weight unless specified otherwise. Examples 1–14 are paste compositions of the invention.

EXAMPLE 1

| Component | Wt % |
|---|---|
| Sodium Hyaluronate | 0.144 |
| Powdered Sugar 10X | 60.144 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 2

| Component | Wt % |
|---|---|
| Chondroitin Sulfate | 4 |
| Sodium Hyaluronate | 0.144 |
| Powdered Sugar 10X | 50.144 |
| Glycerine | 0.7 |
| Xanthan Gum | 0.2 |
| Sodium Benzoate | 0.7 |
| Citric Acid Anhydrous | 0.2 |
| Molasses | 29.5 |
| Water DI | 14.4 |
| TOTAL | 100 |

EXAMPLE 3

| Component | Wt % |
|---|---|
| Glucosamine Sulfate | 40.144 |
| Sodium Hyaluronate | 0.144 |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 4

| Component | Wt % |
|---|---|
| Glucosamine Sulfate | 36.144 |
| Chondroitin Sulfate | 4 |
| Sodium Hyaluronate | 0.144 |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 5

| Component | Wt % |
|---|---|
| Glucosamine Sulfate | 36 |
| Sodium Hyaluronate | 0.144 |
| Manganese Sulfate | 0.144 |
| Powdered Sugar 10X | 24 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 6

| Component | Wt % |
|---|---|
| Chondroitin Sulfate | 4 |
| Sodium Hyaluronate | 0.144 |
| Manganese Sulfate | 0.144 |
| Powdered Sugar 10X | 56 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 7

| Component | Wt % |
|---|---|
| Glucosamine Sulfate | 36 |
| Chondroitin Sulfate | 4 |
| Sodium Hyaluronate | 0.144 |
| Manganese Sulfate | 0.144 |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 8

| Component | Wt % |
|---|---|
| Glucosamine Sulfate | 35 |
| Chondroitin Sulfate | 4 |
| Sodium Hyaluronate | 0.144 |
| Manganese Sulfate | 0.144 |
| Vitamin C | 1 |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 9

| Component | Wt % |
|---|---|
| Glucosamine Sulfate | 36 |
| Chondroitin Sulfate | 4 |
| Sodium Hyaluronate | 0.144 |
| Manganese Sulfate | 0.144 |
| Vitamin D | 200 IU |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 10 -continued

| Component | Wt % |
|---|---|
| Glucosamine Sulfate | 36 |
| Chondroitin Sulfate | 4 |
| Sodium Hyaluronate | 0.144 |
| Manganese Sulfate | 0.144 |
| Ibuprofen | 200 mg |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 11

| Component | Wt % |
|---|---|
| Glucosamine Sulfate | 36 |
| Chondroitin Sulfate | 4 |
| Sodium Hyaluronate | 0.144 |
| Manganese Sulfate | 0.144 |
| Erythromycin | 200 mg |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 12

| Component | Wt % |
|---|---|
| Glucosamine Sulfate | 36 |
| Chondroitin Sulfate | 4 |
| Sodium Hyaluronate | 0.144 |
| Manganese Sulfate | 0.144 |
| Isoxuprine | 100 mg |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 13

| Component | Wt % |
|---|---|
| Glucosamine Sulfate | 40.144 |
| Sodium Hyaluronate | 0.144 |
| Ibuprofen | 800 mg |
| Powdered Sugar 10X | 20 |
| Glycerine | 0.7 |
| Xanthan Gum | 0.2 |
| Sodium Benzoate | 0.7 |
| Citric Acid Anhydrous | 0.2 |
| Molasses | 23.5 |
| Water DI | 14.4 |
| TOTAL | 100 |

EXAMPLE 14 -continued

| Component | Wt % |
|---|---|
| Glucosamine Sulfate | 46.03 |
| Chondroitin Sulfate | 4.60 |
| Sodium Hyaluronate | 0.18 |
| Manganese Sulfate | 0.18 |
| Powdered Sugar 10X | 8.70 |
| Glycerine | 0.7 |
| Xanthan Gum | 0.10 |
| Sodium Benzoate | 0.50 |
| Corn Starch | 0.30 |
| Molasses | 25.00 |
| Water DI | 14.0 |
| TOTAL | 100 |

EXAMPLE 15

The following Example is directed to a gel of HA using CMC as the gelling agent.

| Component | Wt % |
|---|---|
| Sodium Hyaluronate | 1.00 |
| Sodium Carboxymethyl cellulose | 1.00 |
| Propylene glycol | 1.20 |
| Sodium Benzoate | 0.50 |
| Citric Acid | 0.30 |
| Apple Flavor | 1.5 |
| Water DI | 94.5 |
| TOTAL | 100 |

EXAMPLE 16

The following Example is directed to a gel of HA and chondroitin sulphate using CMC as the gelling agent.

| Component | Wt % |
|---|---|
| Sodium Hyaluronate | 1.00 |
| Chondroitin Sulphate | 4.00 |
| Sodium Carboxymethyl cellulose | 1.00 |
| Propylene glycol | 1.20 |
| Sodium Benzoate | 0.50 |
| Citric Acid | 0.30 |
| Apple Flavor | 1.5 |
| Water DI | 90.5 |
| TOTAL | 100 |

EXAMPLE 16

Hard gelatin capsules are prepared using the following ingredients

| Component | Amount mg |
|---|---|
| Sodium Hyaluronate | 100.00 |
| Starch dried | 200.00 |
| Magnesium stearate | 10.00 |
| TOTAL | 310.00 |

EXAMPLE 17

Hard gelatin capsules are prepared using the following ingredients

| Component | Amount mg |
|---|---|
| Sodium Hyaluronate | 100.00 |
| Chondroitin sulphate | 200.00 |
| Starch dried | 200.00 |
| Magnesium stearate | 10.00 |
| TOTAL | 510.00 |

The above ingredients are mixed and filled into hard gelatin capsules in 510 mg quantities.

EXAMPLE 18

Hard gelatin capsules are prepared using the following ingredients

| Component | Amount mg |
|---|---|
| Sodium Hyaluronate | 100.00 |
| Microcrystalline cellulose | 400.00 |
| Silicon Dioxide, fumed | 10.00 |
| Stearic Acid | 5.00 |
| TOTAL | 310.00 |

The components are blended and compressed to form tablets each weighing 665 mg.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations which fall within the spirit and broad scope of the invention.

I claim:

1. An orally administrable Chondroprotective/Restorative composition in gel or paste form for administration to a mammal comprising an effective amount Hyaluronic Acid or its pharmaceutically acceptable salts an a pharmaceutically acceptable gelling or pasting agent capable of forming a gel or a paste selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, cellulose gum carboxymethylcellulose, sodium carboxymethylcellulose and molasses.

2. The Chondroprotective/Restorative composition of claim 1 further including nutritionally effective amounts of a supplement selected from the group consisting of vitamin A, D and E, ascorbic acid, biotin, panthothenic, choline, niacin, pyridoxine, riboflavin, thiamine, calcium, phosphorus, NaCI, copper, iron, manganese, iodine, zinc and combinations thereof.

3. An orally administrable Chondroprotective/Restorative composition comprising:
   (a) an effective amount of Glucosamine sulfate;
   (b) an effective amount Hyaluronic Acid or pharmaceutically acceptable salts thereof; and
   (c) a pharmaceutically acceptable gelling or pasting agent capable of forming a gel or a paste selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, cellulose gum carboxymethylcellulose, sodium carboxymethylcellulose and molasses.

4. The Chondroprotective/Restorative composition of claim 3 further including nutritionally effective amounts of a supplement selected from the group consisting of vitamin A, D and E, ascorbic acid, biotin, panthothenic, choline, niacin, pyridoxine, riboflavin, thiamine, calcium, phosphorus, NaCI, copper, iron, manganese, iodine, zinc and combinations thereof.

5. An orally administrable Chondroprotective/Restorative composition comprising
   (a) an effective amount of Chondroitin sulfate;
   (b) an effective amount of Hyaluronic Acid or pharmaceutically acceptable salts thereof; and
   (c) a pharmaceutically acceptable gelling or pasting agent capable of forming a gel or a paste selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, cellulose gum carboxymethylcellulose, sodium carboxymethylcellulose and molasses.

6. The Chondroprotective/Restorative composition of claim 5 further including nutritionally effective amounts of a supplement selected from the group consisting of vitamin A, D and E, ascorbic acid, biotin, panthothenic, choline, niacin, pyridoxine, riboflavin, thiamine, calcium, phosphorus, NaCI, copper, iron, manganese, iodine, zinc and combinations thereof.

7. An orally administrable Chondroprotective/Restorative composition comprising
   (a) an effective amount of Glucosamine sulfate;
   (b) an effective amount of Chondroitin sulfate;
   (c) an effective amount of Hyaluronic Acid or pharmaceutically acceptable salts thereof; and
   (d) a pharmaceutically acceptable gelling or pasting agent capable of forming a gel or a paste selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, cellulose gum carboxymethylcellulose, sodium carboxymethylcellulose and molasses.

8. The Chondroprotective/Restorative composition of claim 7 further including nutritionally effective amounts of a supplement selected from the group consisting of vitamin A, D and E, ascorbic acid, biotin, panthothenic, choline, niacin, pyridoxine, riboflavin, thiamine, calcium, phosphorus, NaCl copper, iron, manganese, iodine, zinc and combinations thereof.

9. A therapeutic and Chondroprotective/Restorative composition in gel form for oral administration comprising:
   (a) an effective amount of hyaluronic Hyaluronic Acid or its pharmaceutically acceptable salts;
   (b) an effective amount of a therapeutic drug; and
   (c) a pharmaceutically acceptable gelling or pasting agent capable of forming a gel or a paste selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, cellulose gum carboxymethylcellulose, sodium carboxymethylcellulose and molasses.

10. The therapeutic and Chondroprotective/Restorative composition of claim 9 wherein said therapeutic drug is selected from the group consisting of acetaminophen, acetic acid, acetylsalicylic acid, buffered acetylsalicylic acid, albuterol, albuterol sulfate, ethanol isopropanol, allantoin, aloe, aluminum acetate, aluminum carbonate, aluminum chlorohydrate, aluminum hydroxide, alprozolam, amino acids, aminobenzoic acid, amoxicillin, ampicillin, amsacrine, amsalog, anethole, aspartame, atenolol, bacitracin, balsam peru, beclomethasone dipropionate, benzocaine, benzoic acid, benzophenones, benzoyl peroxide, biotin, bisacodyl, bornyl acetate, bromopheniramine maleate, buspirone, caffeine, calamine, calcium, calcium carbonate, calcium casinate, calcium hydroxide, camphor, captopril, cascara sagrada, castor oil, Cephalosporins, cefaclor, cefadroxil, cephalexin, cetylalcohol, cetylpyridinium chloride, chelated minerals, chloramphenicol, chlorcyclizine hydrochloride chlorhexidine gluconate, chloroxylenol, chloropentostatin, chlorpheniramine maleate, cholestyramine resin, choline bitartrate, cimetidine hydrochloride, cinnamedrine hydrochloride, citalopram, citric acid, Clenbuterol, cocoa butter, cod liver oil, codeine and codeine phosphate, clonidine, clonidine hydrochloride, clorfibrate, ciprofloxacin HCl, cyanocobalamin, cyclizine hydrochloride, DMSO, danthron, Dantrium, dexamethazone, dexbrompheniranime maleate, dextromethorphan hydrobromide, diazepam, dibucaine, diclofenac sodium, digoxin, diltiazem, dimethicone, dioxybenzone, diphenhydramine citrate, diphenhydramine hydrochloride, docusate calicum, docusate potassium, docusate sodium, doxycycline hyclate, doxylamine succinate, efaroxan, enalapril, enoxacin, erythromycin, estropipate, ethinyl estradiol, ephedrine, epinephrine bitartrate, erythropoietin, eucalyptol, ferrous fumarate, ferrous gluconate, ferrous sulfate, folic acid, fosphenytoin, Flunixin Meglumine, fluoxetine HCl, furosemide, gabapentan, gentamicin, Gentocin sulfate, gemfibrozil, glipizide, glycerin, glyceryl stearate, griseofulvin, guaifenesin, hexylresorcinol, hydrochlorothiaxide, hydrocodone bitartrate, hydrocortisone, hydrocortisone acetate, 8-hydroxyquinoline sulfate, ibuprofen, indomethacin, inositol, insulin, iodine, ipecac, iron, isoxicam, Isoxuprine, ketamine, Ketofin, koalin, lactic acid, lanolin, lecithin, lidocaine, lidocaine hydrochloride, lifinopril, liotrix, lovastatin, MSM (methylsulfonylmethane), magnesium carbonate, magnesium hydroxide, magnesium salicylate, magnesium trisilocate, mefenamic acid, meclofenanic acid, meclofenamate sodium, medroxyprogesterone acetate, methenamine, mandelate, Methocarbamol, menthol, meperidine hydrochloride, metaproterenol sulfato, methyl nicotinate, methyl salicylate, methylcellulose, methsuximide, metromidazole, metromidazole hydrochloride, metoprolol tartrate, miconazole nitrate, mineral oil, minoxidil, morphine, naproxen, naproxen sodium, nifedipine, neomycin sulfate, Neomycin-Bacitracin, niacin, niacinamide, nicotine, nicotinamide, nitroglycerin, nonoxynol-9, norethindone, norethindone acetate, nystatin, octoxynol, octyl dimethyl PABA, octyl methoxycinnamate, omega-3 polyunsaturated fatty acids, omeprazole, oxolinic acid, oxybenzone, oxtriphylline, para-aminobenzoic acid (PABA), padimate O, paramethadione, Penicillin, pentastatin, peppermint oil, pentaerythriol tetranitrate, pentobarbital sodium, pheniramine maleate, phenobarbital, phenol, phenolphthalein, phenybutazone phenylbutazone, phenylephrine hydrochloride, phenylpropanolamine, phenylpropanolamine hydrochloride, phenytoin, phenelzine sulfate, pinnenol, piroxicam, polymycin B sulfate, potassium chloride, potassium nitrate, prazepam, prednisone, prednisolone, procainamide hydrochloride, procaterol, propoxyphene, propoxyphene HCl, propoxyphene napsylate, pramiracetin, pramoxine, pramoxine hydrochloride, propronolol HCl pseudoephedrine hydrochloride, pseudoephedrine sulfate, pyridoxine, quinapril, quinidine gluconate, quinestrol, ralitoline, ranitadine, resorcinol, riboflavin, salicylic acid, sesame oil, shark liver oil, simethicone, sodium bicarbonate, sodium citrate, sodium fluoride, sodium monofluorophosphate, Sulfa-drugs, sulfanethoxazole, sulfur, tacrine, tacrine HCl, theophylline, terfenidine, thioperidone, trimetrexate, triazolam, timolol maleate, tretinoin, tetracycline hydrochloride, tolmetin, tolnaftate, triamcinolone, triclosan, triprolidine hydrochloride, undecylenic acid, vancomycin, verapamil HCl, vidaribine phosphate, vitamin A, vitamin B, vitamin C, vitamin D, vitamin E, vitamin K, witch hazel, xylometazoline hydrochloride zinc, zinc sulfate, and zinc undecylenate.

11. An oral Chondroprotective/Restorative composition in paste from comprising:
    (a) an effective amount of Hyaluronic Acid or its pharmaceutically acceptable salts; and
    (b) a sufficient amount of molasses to make a paste.

12. The Chondroprotective/Restorative composition of claim 11 further including glucosamine sulfate.

13. The Chondroprotective/Restorative composition of claim 12 further including nutritionally effective amounts of vitamins and minerals.

14. The Chondroprotective/Restorative of claim 11 further including chondroitin sulfate.

15. An orally administrable Chondroprotective/Restorative composition in gel form comprising:
    (a) an effective amount of Hyaluronic Acid or its pharmaceutically acceptable salts;
    (b) water; and
    (c) a sufficient amount of carboxymethylcellulose or its sodium salt to make a gel.

16. The Chondroprotective/Restorative composition of claim 15 further including glucosamine sulfate.

17. The Chondroprotective/Restorative composition of claim 15 further including chondroitin sulfate.

18. The chondroprotective/Restorative composition of claim 15 further including nutritionally effective amounts of vitamins and minerals.

19. The Chondroprotective/Restorative composition of claim 18 further including chondroitin sulfate.

20. A method of treating osteoarthritis, joint effusion, joint inflammation and pain, synovitis, lameness, post operative arthroscopic surgery, deterioration of proper joint function, the reduction or inhibition of metabolic activity of chondrocytes, the activity of enzymes that degrade cartilage, the reduction or inhibition of the production of Hyaluronic acid in a mammal, said method comprising orally administering to said mammal a therapeutically effective amount of the composition of claim 1.

21. The method of claim 20 further including an effective amount of Glucosamine or its pharmaceutically acceptable salts.

22. The method of claim 21 wherein said pharmaceutically acceptable salt is glucosamine sulfate.

23. The method of claim 20 further including an effective amount of chondroitin or its pharmaceutically acceptable salts.

24. The method of claim 23 wherein said pharmaceutically acceptable salt is chondroitin sulfate.

25. The method of claim 20 further including therapeutically effective amounts of glucosamine sulfate and chondroitin sulfate.

26. The method according to claim 20 wherein said hyaluronic acid is uncrosslinked.

27. The method according to claim 26 wherein said therapeutically effective amount of sodium hyaluronate is in the range of 10 mg to 2000 mg.

28. The method according to claim 20 wherein said pharmaceutically acceptable salt is sodium hyaluronate.

* * * * *